United States Patent [19]

Fang

[11] Patent Number: 5,518,590
[45] Date of Patent: May 21, 1996

[54] ELECTROCHEMICAL SENSORS FOR MOTOR OILS AND OTHER LUBRICANTS

[75] Inventor: Jiafu Fang, Conroe, Tex.

[73] Assignee: Pennzoil Products Company, Houston, Tex.

[21] Appl. No.: 263,342

[22] Filed: Jun. 21, 1994

[51] Int. Cl.$^6$ ...................................... G01N 27/26
[52] U.S. Cl. .................. 205/780.5; 204/415; 204/418; 204/412; 324/71.1; 324/439; 422/68.1; 422/82.01; 422/82.02; 422/82.03; 205/782.5; 205/793
[58] Field of Search ..................... 204/153.1, 415, 204/418, 412; 324/71.1, 439; 422/68.1, 82.01, 82.02, 82.03

[56] References Cited

U.S. PATENT DOCUMENTS

| | | | |
|---|---|---|---|
| 2,782,151 | 2/1957 | Suthard | 204/1 T |
| 3,432,403 | 3/1969 | Glass | 204/1 |
| 4,514,263 | 4/1985 | Janata | 204/412 |
| 4,563,263 | 1/1986 | Oyama et al. | 204/418 |
| 4,605,900 | 8/1986 | Moilanen et al. | 204/412 |
| 4,662,996 | 5/1987 | Venkatasetty | 204/415 |
| 4,744,870 | 5/1988 | Kauffman | 204/1 T |
| 4,764,258 | 8/1988 | Kauffman | 204/1 T |
| 4,795,543 | 1/1989 | Stetter et al. | 204/412 |
| 4,889,612 | 12/1989 | Geist et al. | 204/418 |
| 4,985,130 | 1/1991 | Hale | 204/415 |
| 4,995,560 | 2/1991 | Wiles et al. | 204/418 |
| 5,004,532 | 4/1991 | Hale | 204/415 |
| 5,071,527 | 12/1991 | Kauffman | 204/153.1 |
| 5,239,258 | 8/1993 | Kaufmann | 204/153.1 |

OTHER PUBLICATIONS

"Chemical Sensing of Amine Antioxidants in Turbine Lubricants", Richard Price et al., Analyst, Nov. 1991, vol. 116.

*Primary Examiner*—Bruce F. Bell
*Attorney, Agent, or Firm*—Lowe, Price, LeBlanc & Becker

[57] ABSTRACT

A sensitive and rapid electrochemical sensor monitors motor oil deterioration, particularly antioxidation property, by determining the antioxidant and antiwear agent level remaining in an oil formulation. The electrochemical sensor is a two- or three-electrode electrochemical cell having a conductive electrolyte liquid or gel-like interphase over the electrode surfaces. The degree of deterioration of a motor oil in service is monitored by measurements of antioxidation or antiwear capacity of the oil. The electrochemical sensor can be used for monitoring other lubricants and hydrocarbons which contain electroactive additives. The electrochemical sensor allows measurements to be performed in-situ, without any chemical or physical pretreatment of the oil.

20 Claims, 6 Drawing Sheets

ELECTROCHEMICAL SENSORS FOR MOTOR OILS AND OTHER LUBRICANTS

TECHNICAL FIELD

The present invention relates to lubricant formulations and methods of determining the useful service life of lubricant formulations. More specifically, the present invention relates to methods and apparatus for monitoring the concentration of components in lubricant formulations comprising an electrochemical cell having a liquid or gel-like interphase.

BACKGROUND ART

Over the period of its service life, a fully formulated motor oil deteriorates and becomes ineffective for protecting the moving and rubbing parts of an engine. Under normal operations, deterioration occurs mostly due to thermal break-down of the oil. In the early stages of service life, there exist adequate amounts of antioxidant and antiwear agents in an oil formulation. In simplified situations, the antioxidants provide protection for other constituents of the oil formulation, mainly the base oil, from thermal oxidation reactions, whereas the antiwear agents (zinc dialkyldithiophosphates (ZDDP) in most current motor oil formulations) protect the lubricated parts of the engine by chemically and/or physically being adsorbed on the surfaces of these parts to form a protective film. However, both the antioxidant and antiwear agents are consumed steadily as the service time increases.

As the service time increases, a point will be reached at which the level of the antioxidants in the oil formulation will be so low that they will no longer protect the oil from undergoing rapid oxidation reactions. Thereafter, the viscosity of the oil increases drastically over a very short period of time due to the massive formation of polymeric oxidation products. This will lead to engine damage if the oil is not changed immediately. Obviously, knowing the level of the antioxidants and its change in the oil is critically important for monitoring the oil quality during its service life.

Electrochemical methods are versatile, sensitive, and allow easy control of experimental conditions. Much effort has been executed to develop a simple but sensitive device which can be used to monitor deterioration of a motor oil in-situ. However, some of the techniques developed to date require chemical separations before an oil sample can be analyzed, are not very sensitive or have a slow response time.

An electrochemical method is reported by Richard J. Price et al., "Chemical Sensing of Amine Anti-Oxidants in Turbine Lubricants", Analyst, November, 1991, Vol. 116, pages 1121–1123. Price et al. disclose an electrical chemical sensor for oil formulations comprising a 3-electrode arrangement having a silver wire acting as a pseudo reference, a platinum wire functioning as a counter electrode and a platinum microdisc as a working electrode. The electrodes were coated with a polymer film cast from a solution of poly(ethylene oxide) and $LiClO_4$ in acetonitrile-methanol.

Although the electrode was able to determine the presence of amine antioxidants in turbine lubricants, the electrode suffers from various disadvantages in that it is not a very good conductor, the response time is long and it is not very sensitive to antioxidant or antiwear concentrations.

Accordingly, a need exists in the art for an electrochemical sensor for motor oils which is sensitive and have a quick response time.

DISCLOSURE OF THE INVENTION

It is accordingly an object of the present invention to provide an improved method of monitoring the useful service life of lubricants by detecting electroactive components in nonconducting environments.

This objective is achieved by providing an electrochemical cell having a liquid or gel-like electrolyte interphase through which electroactive components in a nonconducting environment can pass to reach the working electrode of the electrochemical cell.

According to these and other objects of the present invention which will become apparent as the description thereof proceeds, the present invention provides a method of detecting electroactive components in a nonconductive environment which involves:

a) providing an electrochemical sensor having at least two electrodes and a conductive liquid or gel-like electrolyte interphase covering each of the at least two electrodes;

b) contacting the conductive liquid or gel-like electrolyte interphase with a nonconductive environment containing electroactive components;

c) allowing the electroactive components in the nonconductive environment to pass through the conductive liquid or gel-like electrolyte interphase of the electrochemical cell; and d) utilizing the electrochemical cell to measure the concentration of the electroactive components in the conductive interphase.

According to a preferred embodiment, the nonconductive environment comprises a lubricant, such as a motor oil or a compressor oil. The electroactive components include conventional additives contained in lubricants such as antioxidants, e.g, dioctydiphenylamine, and antiwear agents, e.g, zinc dialkydithiophosphate.

The present invention also provides for a sensor for detecting electroactive components in a nonconductive environment which comprises:

at least two electrodes; and a conductive interphase covering the at least two electrodes, the conductive interphase comprising a liquid or gel-like electrolyte solution which is selectively permeable to electroactive components of a nonconducting environment.

In addition to a two-electrode configuration, a three-electrode configuration can be utilized. Also, a hydrophilic membrane which covers the conductive liquid or gel-like electrolyte interphase is provided in a preferred embodiment.

BRIEF DESCRIPTION OF DRAWINGS

The present invention will be described hereafter with reference to the attached drawings which are given by way of non-limiting examples only, in which.

DESCRIPTION OF THE INVENTION

The present invention involves the development of an improved electrochemical sensor for oil deterioration monitoring which is more sensitive and has a shorter response time than those of the prior art. Unlike the viscosity and dielectric constant techniques which measure an overall property of the oil, the electrochemical sensor of the present invention monitors changes in the level of antioxidant and antiwear agents whose presence beyond a certain concentration is critical to the performance of the oil. Since the signal response of the electrochemical sensor is directly related to specific chemical components in the oil, it has been found to provide direct information about the stressed degree of extent of the oil. Therefore, the electrochemical sensor of the present invention allows the operator of the engine to follow the deterioration course of the oil and to be aware when the oil needs to be changed before subsequent damage to the engine occurs.

The electrochemical sensor of the present invention is and can be directly used in fully formulated motor oils and other lubricant formulations. It allows one to quickly monitor oil deterioration by determining changes in antioxidant and antiwear concentrations. The electrochemical sensor of the present invention can be utilized for on-line monitoring of motor oil conditions in an engine or motor and for quality control in a lubricant, e.g., motor oil manufacturing process. Applications of the electrochemical sensor also include other various hydrocarbon fluids containing electroactive additives, such as compressor oils, turbine engine oils, etc.

To apply electrochemical techniques for direct determination of antioxidant and antiwear agents in a motor oil or other lubricants, the first and most critical thing one encounters is the low conductivity problem of the oil. If an electrode, metallic or nonmetallic, is inserted directly into a motor oil, the electrode surface becomes covered immediately by a nonconducting film of the oil, making it impossible to carry out any electrochemical measurements.

To overcome this problem, the present invention involves modifying the electrode surface in a manner which creates a liquid or gel-like interfacial phase between the solid electrode and the oil phase. The liquid or gel-like interphase is electrically conductive and permeable to antioxidant and antiwear additives and impermeable to nonpolar oily components and high polymers. The antioxidant and antiwear additives which enter and pass through the liquid or gel-like electrolyte interphase then reach the electrode surface and react there, causing a current to -pass through the electrochemical cell when the applied electrode potential is appropriate.

The liquid or gel-like interphase between the electrode surface and the oil phase is an electrolyte solution, preferably comprising a sodium or lithium perchlorate ($LiClO_4$) in acetonitrile (ACN) as the interphase. It is able to effectively and selectively extract the components of interest and has a large electrochemical window and a high conductivity. In particular, this solution was found to be very useful for oxidation reactions at room temperature since both the electrolyte $LiClO_4$ and solvent ACN are stable toward electrode oxidation. Other useful electrolytes include organic salts which can render a large electrochemical potential window, high electric conductivity, substantial solubility in the given solvent. Examples of such preferred organic salts include, but are not limited to, tetraalkylammonium tetrfluoroborate (TAATFB) and hexafluorophosphate. The electrolytes are used in a concentration of about $10^{-4}$ up 0.1M.

The solvent employed in the interphase can be any polar solvent or mixture of solvents which has a medium or high dielectric constant, a large electrochemical window, is able to solubilize the electrolyte chosen, to selectively extract the electroactive components in the oil phase while not miscible with the oil phase. Preferred solvents include, but are not limited to, ACN, low carbon number alcohols such as methanol, ethanol.

Detections of antioxidant and antiwear agents using electrochemical techniques are most conveniently carried out by application of oxidation potentials. The reduction mode is seldom used because these additives are typically alkylated phenols and aromatic amines which are readily oxidized at an electrode but otherwise difficult to reduce.

A typical electrochemical cell normally consists of three electrodes, including a working electrode (WE), a counter electrode (CE), and a reference electrode (RE); however, according to the present invention, a two-electrode configuration may also be used. The working electrode preferably comprises a glassy carbon rod having a diameter of either 1 mm or 3 mm; however, any inert material which will conduct electricity is useful. For example, gold, platinum or other metals may be substituted. The counter electrode is preferably made of the same material as the working electrode or may be platinum wire. The reference electrode may be either AgCl/Ag in a 3M NaCl aqueous solution saturated with AgCl, or a silver wire dipped into a solution of 0.1M $AgNO_3$ in ACN. In the embodiment wherein two electrodes are used, the counter electrode also functions as the reference electrode in a known manner.

Figure 1:
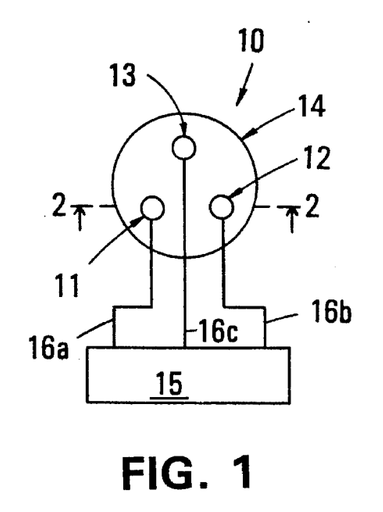
FIG. 1 is a schematic diagram of an electrochemical cell according to one embodiment of the present invention.

FIG. 1 is a schematic diagram of an electrochemical cell according to one embodiment of the present invention. The electrochemical cell 10 includes a working electrode 11 a counter electrode 12 and a reference electrode 13. Each of the electrodes is supported by support means 14 which is preferably made of a suitable insulating material such as a plastic. The support means 14 may be any convenient shape depending upon the application of the electrochemical cell. For example, a cylindrically shaped support, as shown, may be convenient for insertion into a port of an engine where the electrodes may be in contact with a motor oil circulating in the engine. The basic function of the support means 14 is to provide a surface at which the ends of the electrodes are positioned with respect to one another as discussed below.

Each of the electrodes is connected to a conventional measuring apparatus 15, by leads 16a, 16b, and 16c. The measuring apparatus 15 operates according to one or more known voltammetry or other electrochemical techniques.

Figure 2:
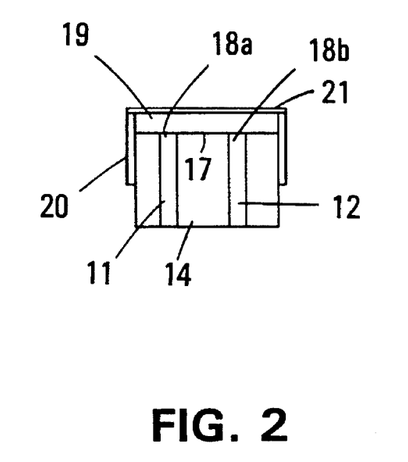
FIG. 2 is a schematic elevational view of the electrochemical cell of FIG. 1 taken along section line 2—2.

FIG. 2 is a schematic elevational view of the electrochemical cell of FIG. 1 taken along section line 2—2 of FIG.

1. As shown in FIG. 2, support means 14 provides a surface means 17 at which the ends of each of the electrodes are located. The working electrode 11 and counter electrode 12 are shown positioned so that their ends 18a and 18b are approximately flush with surface means 17 of the support means 14. Electrodes 11 and 12 pass through support means 14 so that electrical leads (not shown in FIG. 2) can be attached to the electrodes. Alternatively, electrical leads may connect to the electrode within support means 14.

Liquid or gel-like interphase 19 is preferably immobilized by a sleeve means 20 comprising a plastic such as Teflon or PEEK (polyether ether ketone). A hydrophilic membrane 21 such as nylon 66 is preferably provided to contain liquid or gel-like interphase 19. The thickness of the liquid or gel-like interphase is controlled by the quantity of conducting medium applied. Typically, the interphase thickness affects the response time of the electrochemical sensor.

Sleeve means 20 may be a simple cylindrical piece of a nonconducting material such as plastic as shown in FIG. 2. In other embodiments, the sides of the sleeve 20 may include notches or other cut-outs to permit membrane 21 to extend over the sides of the sleeve 20. Sleeve means 20 and the membrane 21 may be secured to support means 14 by any convenient manner including chemical bonding, e.g., cementing or by mechanical fasteners, including press-tight fitting.

Many different known electrochemical methods may be used for operating the electrochemical sensor of the present invention. For example, voltammetric techniques such as cyclic voltammetry (CV), square wave voltammetry (SWV), linear scan voltammetry (LSV), differential pulse voltammetry (DPV), normal pulse voltammetry (NPV), and time-based techniques such as modified chronoamperometry (MCA), have been successfully used.

An EG&G PARC potentiostat Model 273 is preferably used for performing the electrical measurements in testing the electrochemical sensor of the present invention. However, any potentiostat able to provide one of the aforementioned techniques may be used.

In the MCA mode, a positive potential, $E_1$, which is anodic enough to cause the interested component(s) to react at the maximum rate (diffusion controlled) is applied for a period of $\tau_1$. A current reading is sampled near the end of the $\tau_1$ period so that the effect of double layer charging current is minimized. Thereafter, a second potential $E_2$, at which no electrode reactions occur, is applied for a period $\tau_2$. No current reading is taken during the period $\tau_2$. This process is preferably repeated many times, depending on how many data points one desires to collect for the test sample. $\tau_2$ is typically much longer than $\tau_1$ and the ratio between them may be adjusted.

The sampled current is proportional to the concentration of the component(s) responsible for the electrode reaction(s), i.e., the antioxidant or antiwear agent concentration in the interphase; which in turn is proportional to their concentrations in the oil phase. The MCA method is particularly convenient for measuring the time response of the electrochemical sensor since the method reveals the oxidation current as a function of time.

A preferred method comprises conducting a blank test on the interphase using one or -more of the above techniques before the electrochemical sensor is dipped into an oil sample or an oil sample is placed on the top of the tip of the electrochemical sensor. The same electrochemical technique(s) as that used in the blank test is then used to measure signal response due to antioxidant or antiwear additives from the oil sample. The signal response is repeatedly monitored for a certain period of time until a maximum value is reached.

The time required to reach the maximum response after the oil sample is loaded is typically less than 10 minutes, depending on the properties of the sample and the thickness of the liquid interphase. For example, a sample having a higher viscosity will take a longer time to establish equilibrium than a sample having a lower viscosity, other things being equal.

Features and characteristics of the present invention will be illustrated in the following examples to which the present invention is not to be considered as limited. In the examples and throughout, percentages are by weight unless otherwise indicated.

In the following examples, several oil samples were tested using the three-electrode electrochemical sensor described above. In the examples, tests were performed on oils ranging from simple compositions to more complex, fully formulated motors oils.

EXAMPLE 1

In this example, oils composed of polyalphaolefin (PAO) and antioxidant p,p'-dioctyldiphenylamine) were tested utilizing the electrochemical sensor of the present invention. p,p'-dioctyldiphenylamine is commonly used in motor oils and other lubricants. Synthetic polyalphaolefin (PAO) having a viscosity of 6 centistokes at 100° C. (PAO 6) was used as the base stock. Three samples respectively containing 0.025%, 0.1% and 0.3% p,p'-dioctyldiphenylamine were prepared and tested using the electrochemical sensor of the present invention. SWV and CV techniques were employed.

Figure 3:
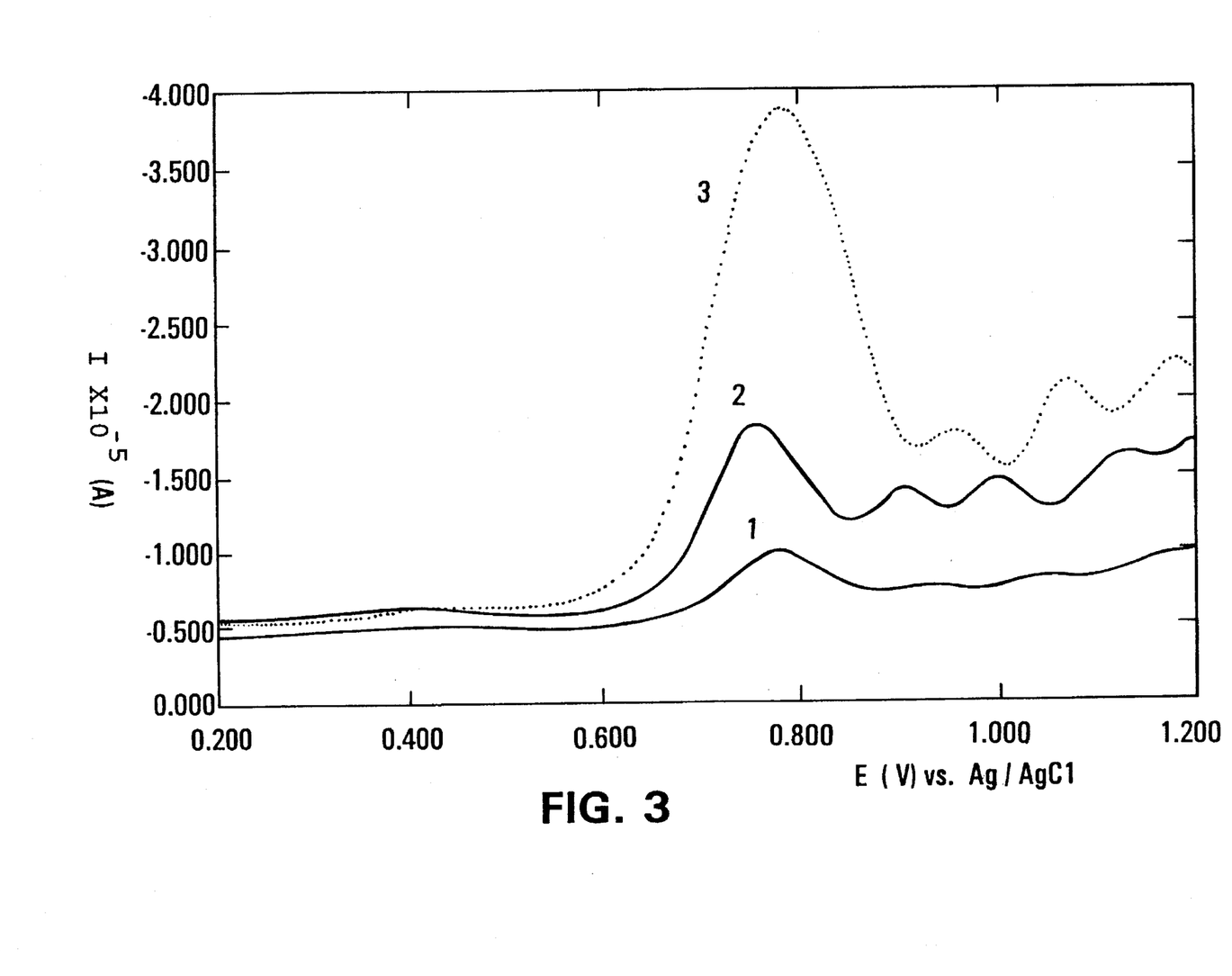
FIG. 3 shows square wave voltammograms of polyalphaolefin oils containing the antioxidant p,p'-dioctyldiphenylamine at 0.025% (curve 1), 0.1% (curve 2), and 0.3% (curve 3).
Figure 4:
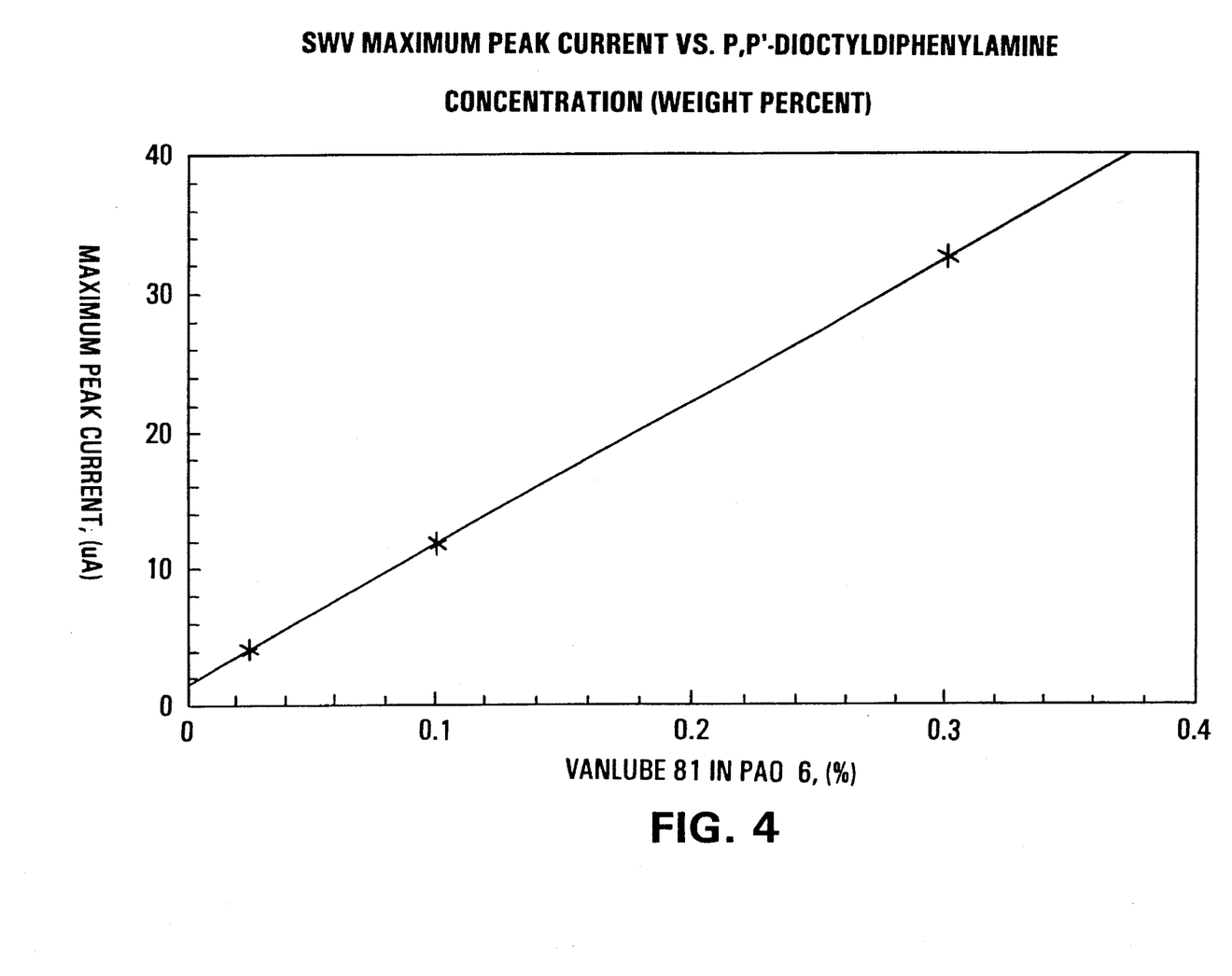
FIG. 4 is a plot of square wave peak current vs. p,p'-dioctyldiphenylamine concentration (weight percent) for the data in FIG. 3.

For each sample, a CV or SWV experiment was repeated every few minutes until a maximum response was obtained. FIG. 3 shows the square wave voltammograms for these samples. The potential values were reported versus the Ag/AgCl (3M NaCl) reference electrode. Curves 1, 2 and 3 respectively correspond to p,p'-dioctyldiphenylamine concentrations of 0.025%, 0.1% and 0.3%. Each curve represents the maximum response for each sample. As expected, the higher the antioxidant concentration, the greater the signal response. The net height of the major peak at about 0.78 V plotted as a function of the antioxidant concentration is shown in FIG. 4. The response increases linearly with the antioxidant concentration. CV experiments gave similar results.

EXAMPLE 2

In this example an oil composed of polyalphaolefin (PAO) and zinc dialkyldithiophosphate (ZDDP) was tested utilizing the electrochemical sensor of the present invention. Virtually all commercial motor oil formulations contain ZDDP as the primary antiwear additive as it also possesses antioxidation properties.

Figure 5:
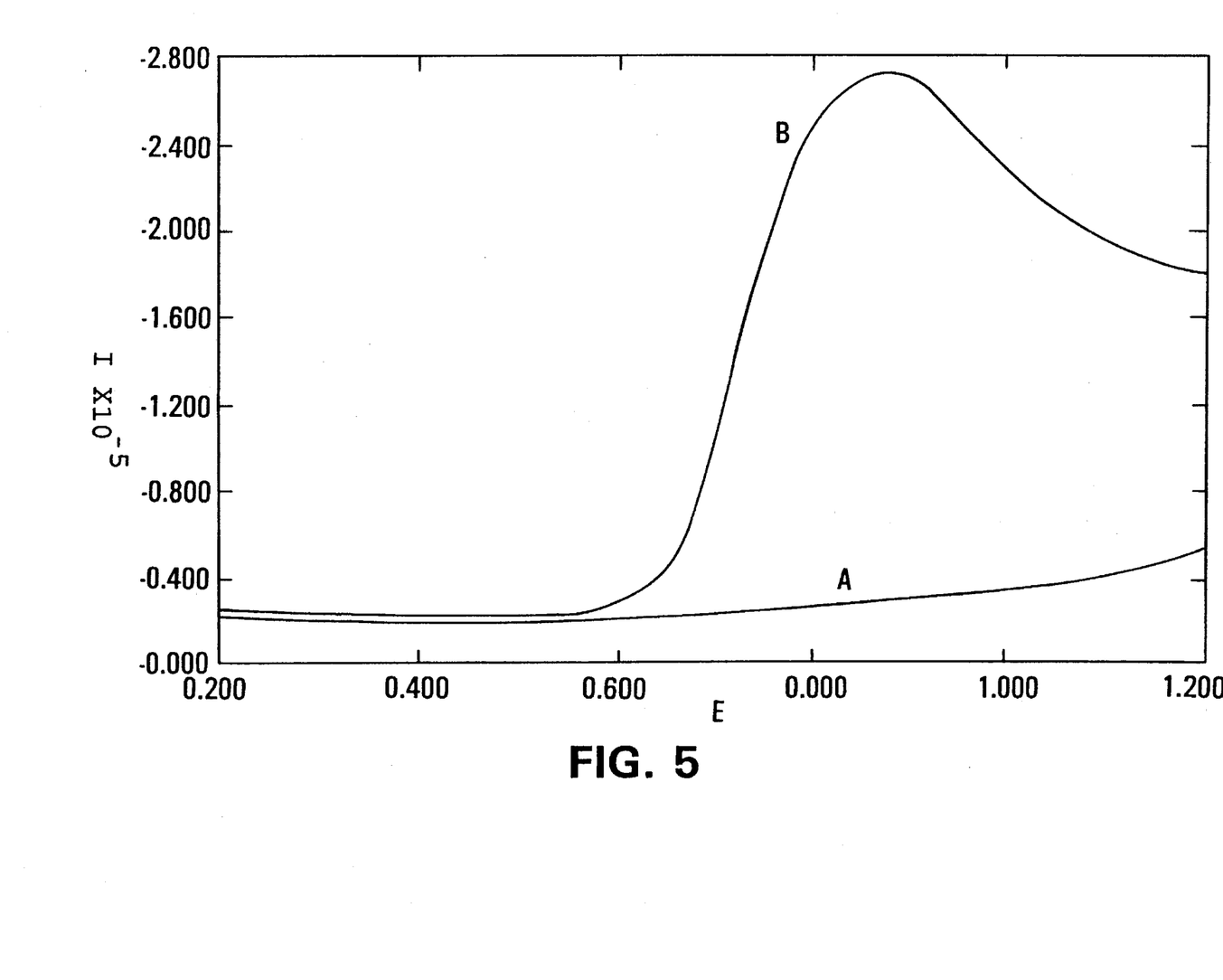
FIG. 5 shows square wave voltammograms of polyalphaolefin oils containing zinc dialkyldithiophosphate. Curve A is a blank test and curve B includes 1.5% zinc dialkyldithiophosphate.

FIG. 5 shows the results obtained from a sample oil consisting of 1.5% ZDDP in PAO 6. Curve A is the square wave voltammogram of the blank interphase. After the oil sample was topped on the electrochemical sensor surface for about 3 minutes, the maximum response was obtained and depicted by curve B. A peak was observed at about 0.85 V. This example demonstrates that ZDDP is readily detectable using the electrochemical sensor of the present invention.

EXAMPLE 3

In this example a sample of a commercially available motor oil, designated as M1 15W-50, was tested utilizing the electrochemical sensor of the present invention. M1 15W-50 is a fully synthetic motor oil whose base stock is polyalphaolefin. Three samples were tested. Sample A was an unused portion of the oil. Samples B and C had undergone an engine test called DEPOX for a period of 30 and 60 hours respectively. The total engine test time was 70 hours. CV and SWV techniques were used in this example. Both techniques gave similar results. Since SWV generates simpler voltammograms (one way scanning) than CV (two-way scanning), only the SWV results of the three samples of this example are presented in FIG. 6 for the sake of clarity.

Figure 6:
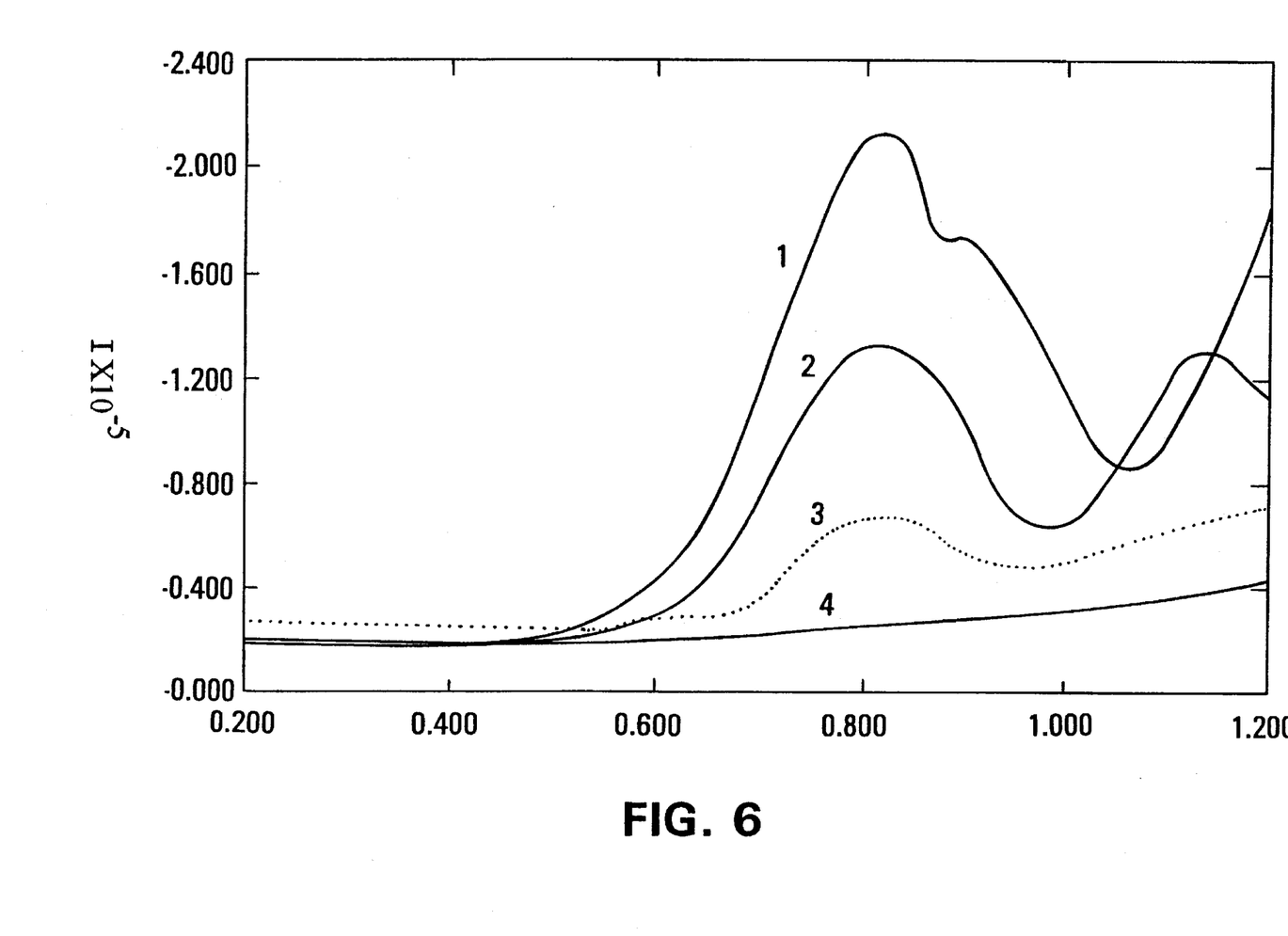
FIG. 6 shows square wave voltammograms of several tested samples of a commercial synthetic motor oil (designated as M1 15W-50) from a Depox Engine Test. Curve 1 is for unused oil. Curve 2 is for oil tested for 30 hours. Curve 3 is for oil tested for 60 hours. Curve 4 is a blank test.

In FIG. 6, curve 1 was obtained from sample A, curve 2 from sample B, curve 3 from sample C, and curve 4 from the blank (conducting interphase). As is apparent, the overall response (oxidation current) decreases as engine test time increases. An obvious shoulder at about 0.9 V on the voltammogram of the unused oil sample diminishes for the 30- and 60-hour samples. A peak current response apparently appeared beyond 1.2 V from the unused sample. This peak shifted to a lower potential at about 1.1 V for the 30-hour sample and disappeared for the 60-hour sample, indicating that the antioxidant or antiwear agent(s) responsible for this peak was completely depleted after 60 hours of engine test. Similarly, the major peak response at about 0.8 V was decreasing (linearly) with engine test time, the net height of the 60-hour sample being about 15% of that of the unused sample.

EXAMPLE 4

Figure 7:
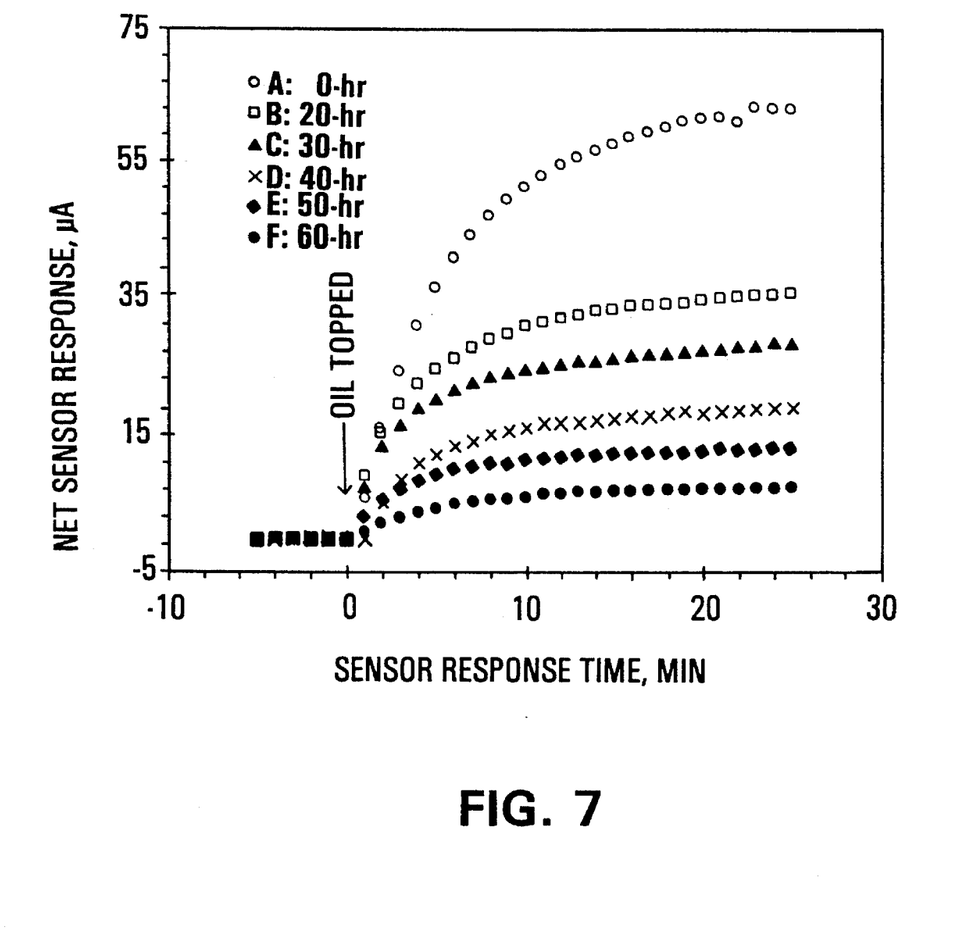
FIG. 7 depicts data of modified chronoamperometry (MCA) obtained from a set of used oil samples of an engine test. As indicated by the legend, the curves, from top to bottom, represent respectively the 0-hour, 20-hour, 30-hour, 40-hour, 50-hour, and 60-hour samples. Each curve shows the electrochemical sensor output as a function of time after the oil sample is brought to contact with the sensor.

In this example a set of used oil samples from an industrial DEPOX engine test was tested using the electrochemical sensor of the present invention. The engine tested oil was a commercial 15W-50 oil. Samples A to F were samples taken at 0-hour, 20-hour, 30-hour, 40-hour, 50-hour, and 60-hour, respectively. the modified chronoamperometry (MCA) technique was employed in the study of these used oil samples. Experimental results are shown in FIG. 7. In this figure, curves A to F, respectively, represent the response of the electrochemical sensor of the present invention for samples A to F. These curves were determined using the following parameters: $E_1=1000$ mV, $\tau_1=1$ second, $E_2=200$ mV, and $\tau_2=59$ seconds. The potentials $E_1$ and $E_2$ were versus the Ag/AgCl reference electrode. As is shown in the figure, the electrochemical sensor of the present invention was monitored for several minutes before the oil sample was brought into contact with the sensor. The output of the sensor during this period of time was a flat residual current. After the oil sample was topped on the surface of the tip of the sensor, response from the sensor was seen immediately. The output current (oxidation current) increased quickly and nearly reached a saturated value within a few minutes for most of the samples except sample A in which the antioxidant and antiwear agents stayed at their original concentrations. How soon the response of the electrochemical sensor of the present invention reached the saturated value depended on the concentration of the antioxidant and antiwear agents in the oil phase and the thickness of the conducting interphase. The lower the concentration of the antioxidant and antiwear agents in the oil phase and the thinner the conducting interphase, the faster the response, other conditions being kept constant. From the figure, one sees that the saturated response of the electrochemical sensor of the present invention was a strong function of engine test time. As the engine test was extended, the amount of consumption of antioxidant and antiwear agents increased. Therefore the response of the sensor diminished since this response is directly proportional to the amount of antioxidant and antiwear agents existing in the oil phase. In the antioxidant and antiwear agents in the oil were completely depleted, no net response from the sensor would be observed. Clearly, this example again demonstrates that the electrochemical sensor of the present invention can be used to monitor the deterioration of an engine oil or other lubricants containing electroactive components such as antioxidant and antiwear agents.

In addition to the oil samples tested in the above examples, other fully formulated motor oils, a refrigeration oil (compressor oil), a turbine engine oil, and rusting oil were also tested using the electrochemical sensor of the present invention. All oils tested produced adequate signal responses for monitoring purposes. All the tests demonstrate that the electrochemical sensor of the present invention is a versatile general device able to detect electroactive additives in many nonconductive environments without sample pretreatment.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims which follow.

What is claimed is:

1. A method of detecting electroactive components in a nonconductive environment which comprises:

a) providing an electrochemical sensor having at least two electrodes and a conductive liquid or gel interphase covering each of said at least two electrodes, said liquid or gel interphase is positioned between said at least two electrodes and a nonconductive environment containing electroactive components;

b) contacting the conductive liquid or gel interphase with said nonconductive environment containing electroactive components;

c) allowing said electroactive components in said nonconductive environment to pass through the conductive liquid or gel interphase of the electrochemical cell; and d) utilizing the electrochemical cell to measure the concentration of said electroactive components in the conductive interphase.

2. The method according to claim 1, wherein said conductive liquid or gel interphase comprises an electrolyte solution.

3. The method according to claim 2, wherein said electrolyte comprises a lithium or sodium perchlorate salt solution, or other organic salts, of concentration between $10^{-4}$M to 1M.

4. The method according to claim 3, wherein said salt is soluble in an organic solvent.

5. The method according to claim 4, wherein said organic solvent comprises a polar solvent or mixture of solvents which has a medium or high dielectric constant, a large electrochemical window, solubilizes the electrolyte chosen, and selectively extracts the electroactive components in an oil phase while not being miscible with the oil phase.

6. The method according to claim 5, wherein said organic solvent is selected from the group consisting of acetonitrile and $C_1$ to $C_5$ alkanols.

7. The method according to claim 6, wherein the $C_1$ to $C_5$ alkanols are methanol, ethanol or propanol.

8. The method according to claim 3, wherein said salt comprises tetrabutyl ammonium tetrafluoro borate and is present at a concentration of about $10^{-3}$M up to 10 hu −1M.

9. The method according to claim 2, wherein said electrolyte comprises lithium or sodium perchlorate in an acetonitrile solvent.

10. The method according to claim 1, wherein said nonconductive environment comprises a hydrocarbon lubricant.

11. The method according to claim 1, wherein said electroactive components comprise antioxidant and/or antiwear agent.

12. The method according to claim 1, further comprising a hydrophilic membrane covering said conductive liquid or gel interphase.

13. A sensor for detecting electroactive components in a nonconductive environment which comprises:

at least two electrodes; and a liquid conductive or gel conductive interphase covering said at least two electrodes, said conductive liquid or gel conductive interphase comprising an electrolyte solution which is selectively permeable to electroactive components of a nonconducting environment.

14. The sensor according to claim 13, wherein said electrolyte solution is selectively permeable to antioxidants and antiwear agents.

15. The sensor according to claim 13, wherein said electrolyte comprises a lithium or sodium perchlorate salt solution.

16. The sensor according to claim 15, wherein said salt is soluble in an organic solvent.

17. The sensor according to claim 16, wherein said electrolyte comprises a solution of lithium perchlorate salt in an acetonitrile solvent.

18. The sensor according to claim 7, wherein said at least two electrodes comprise three electrodes.

19. The sensor according to claim 7, further comprising a hydrophilic membrane covering said conductive liquid or gel interphase.

20. The sensor according to claim 19, wherein said salt is tetrabutyl ammonium tetrafluoro borate and is present at a concentration of about $10^{-3}$M up to $10^{-1}$M.

* * * * *